(12) United States Patent
McPherson et al.

(10) Patent No.: US 12,203,941 B2
(45) Date of Patent: Jan. 21, 2025

(54) METHODS AND COMPOSITIONS FOR DIAGNOSIS AND PROGNOSIS OF RENAL INJURY AND RENAL FAILURE

(71) Applicant: ASTUTE MEDICAL, INC., San Diego, CA (US)

(72) Inventors: Paul McPherson, Encinitas, CA (US); Lakhmir S. Chawla, McLean, VA (US)

(73) Assignee: Astute Medical, Inc., San Diego, CA (US)

( * ) Notice: Subject to any disclaimer, the term of this patent is extended or adjusted under 35 U.S.C. 154(b) by 1235 days.

(21) Appl. No.: 16/806,653

(22) Filed: Mar. 2, 2020

(65) Prior Publication Data

US 2020/0271669 A1    Aug. 27, 2020

Related U.S. Application Data

(63) Continuation of application No. 14/896,270, filed as application No. PCT/US2014/041156 on Jun. 5, 2014, now abandoned.

(60) Provisional application No. 61/862,913, filed on Aug. 6, 2013, provisional application No. 61/831,294, filed on Jun. 5, 2013.

(51) Int. Cl.
| | | |
|---|---|---|
| *G01N 33/53* | (2006.01) | |
| *A61B 5/145* | (2006.01) | |
| *A61K 31/341* | (2006.01) | |
| *G01N 33/493* | (2006.01) | |
| *G01N 33/68* | (2006.01) | |
| *G01N 33/70* | (2006.01) | |

(52) U.S. Cl.
CPC ..... *G01N 33/6893* (2013.01); *A61B 5/14546* (2013.01); *A61K 31/341* (2013.01); *G01N 33/493* (2013.01); *G01N 33/70* (2013.01); *G01N 2333/65* (2013.01); *G01N 2333/96486* (2013.01); *G01N 2800/347* (2013.01); *G01N 2800/50* (2013.01); *G01N 2800/52* (2013.01); *G01N 2800/60* (2013.01)

(58) Field of Classification Search
CPC .. G01N 33/6893; G01N 33/493; G01N 33/70; G01N 2333/65; G01N 2333/96486; G01N 2800/347; G01N 2800/50; G01N 2800/52; G01N 2800/60; A61B 5/14546; A61K 31/341; Y02A 50/30
See application file for complete search history.

(56) References Cited

U.S. PATENT DOCUMENTS

| | | | |
|---|---|---|---|
| 5,480,792 A | 1/1996 | Buechler et al. | |
| 5,525,524 A | 6/1996 | Buechler et al. | |
| 5,571,698 A | 11/1996 | Ladner et al. | |
| 5,631,171 A | 5/1997 | Sandstrom et al. | |
| 5,679,526 A | 10/1997 | Buechler et al. | |
| 5,824,799 A | 10/1998 | Buechler et al. | |
| 5,851,776 A | 12/1998 | Valkirs | |
| 5,885,527 A | 3/1999 | Buechler | |
| 5,922,615 A | 7/1999 | Nowakowski et al. | |
| 5,939,272 A | 8/1999 | Buechler et al. | |
| 5,947,124 A | 9/1999 | Buechler et al. | |
| 5,955,377 A | 9/1999 | Maul et al. | |
| 5,985,579 A | 11/1999 | Buechler et al. | |
| 6,019,944 A | 2/2000 | Buechler | |
| 6,057,098 A | 5/2000 | Buechler et al. | |
| 6,113,855 A | 9/2000 | Buechler | |
| 6,143,576 A | 11/2000 | Buechler | |
| 2005/0158729 A1 | 7/2005 | Stanton et al. | |
| 2006/0115430 A1 | 6/2006 | Cantor | |
| 2007/0184439 A1 | 8/2007 | Guilford et al. | |
| 2007/0249002 A1 | 10/2007 | Hu et al. | |
| 2009/0130693 A1 | 5/2009 | Bassi et al. | |
| 2010/0121220 A1 | 5/2010 | Nishtala | |
| 2011/0046516 A1 | 2/2011 | Paz et al. | |

FOREIGN PATENT DOCUMENTS

| | | | |
|---|---|---|---|
| CN | 102781326 | 11/2012 | |
| EP | 1808694 | 7/2007 | |
| WO | WO 2011/075744 | 6/2011 | |
| WO | WO 2011/097539 | 8/2011 | |
| WO | WO 2013/078253 | 5/2013 | |
| WO | WO2013086359 | * 6/2013 | ............. G01N 33/53 |

OTHER PUBLICATIONS

Ho et al. (Critical Care and Resuscitation 2003; 5: 97-102).*
Alge et al., "Urinary Angiotensinogen and Risk of Severe AKI," Clin J Am Soc Nephrol, Feb. 2013, 8:184-193—with Supplementary Material, 36 pages total.
Arendshorst et al., "Pathogenesis of Acute Renal Failure following Temporary Renal Ischemia in the Rat," Circ Res, Nov. 1975, 37:558-568.
Baek et al., "Early Prediction of Acute Renal Failure and Recovery: II. Renal Function Response to Furosemide," Annals of Surgery, Nov. 1973, 178(5):605-608.
Baek et al., "Early Prediction of Acure Renal Failure and Recovery: 1. Sequential Measurements of Free Water Clearance," Ann Surg, Mar. 1973, 177(3):253-258.

(Continued)

*Primary Examiner* — Carmencita M Belei

(57) ABSTRACT

It is an object of the present invention to provide a combination of a functional assessment of renal function together with biomarker results in order to improve assessment of patient at risk of, or having, an acute kidney injury. A loop diuretic such as furosemide inhibits luminal active chloride transport throughout the thick ascending limb of Henle, thereby preventing sodium reabsorption and resulting in natriuresis and increased urine flow. Loop diuretic-induced increases in urine output might be a method to assess the integrity of the renal tubular function in the setting of early AKI, and so a kidney's response, or lack thereof, to a diuretic challenge as a clinical assessment of tubular function can identify patients with severe tubular injury before it is clinically apparent (e.g. a rise in creatinine).

6 Claims, No Drawings

(56) References Cited

OTHER PUBLICATIONS

Bagshaw et al., "The SPARK Study: a phase II randomized blinded controlled trial of the effect of furosemide in critically ill patients with early acute kidney injury," Trials, 2010, 11:50, 10 pp.

Bagshaw et al., "Urine biochemistry in septic and non-septic acute kidney injury: a prospective observational study," J Crit Care, Aug. 2013, 28(4):371-378.

Bagshaw et al., "A multi-centre evaluation of the RIFLE criteria for early acute kidney injury in critically ill patients," Nephrol Dial Transplant, 2008, 23:1203-1210.

Bellomo et al., "Acute kidney injury," Lancet, Aug. 25, 2012, 380:756-766.

Bellomo et al., "Acute renal failure—definition, outcome measures, animal models, fluid therapy and information technology needs: the Second International Consensus Conference of the Acute Dialysis Quality Initiative (ADQI) Group," Crit Care, Aug. 2004, 8(4):R204-212.

Bird et al., "Ischemic Acute Renal Failure and Antioxidant Therapy in the Rat, The Relation between Glomerular and Tubular Dysfunction," J Clin Invest, May 1988, 81:1630-1638.

Bonventre, "Diagnosis of Acute Kidney Injury: From Classic Parameters to New Biomarkers," Contrib Nephrol, 2007, 156:213-219.

Bowman, "Renal secretion of [35-S]furosemide and its depression by albumin binding," Am J Physiol, Jul. 1975, 229(1):93-98.

Brater et al., "Azosemide, a "loop" diuretic, and furosemide," Clin Pharmacol Ther. Apr. 1979;25(4):435-439.

Burg et al., "Furosemide effect on isolated perfused tubules," Am J Physiol, Jul. 1973, 225(1):119-124.

Chawla et al., "Accute Kidney Injury in 2011: Biomarkers are transforming our understanding of AKI," Nat Rev Nlephrol, Feb. 2012, 8:68-70.

Chawla et al., "Development and Standardization of a Furosemide Stress Test to Predict the Severity of Acute Kidney Injury," Critical Care, Sep. 20, 2013, 17(5):R207.

Chawla et al., "Identifying critically ill patients at high risk for developing acute renal failure: A pilot study," Kidney Int, 2005, 68:2274-2280.

Chawla et al., "Urinary Sediment Cast Scoring Index for Acute Kidney Injury: A Pilot Study," Nephron Clin Pract, 2008, 110:c145-c150.

Chennavasin et al., "Pharmacodynamic analysis of the furosemide-probenecid interaction in man," Kidney Int, 1979, 16:187-195.

Chertow et al., "Acute Kidney Injury, Mortality, Length of Stay, and Costs in Hospitalized Patients," J Am Soc Nephrol, 2005, 16:3365-3370.

Coca et al., "Chronic kidney disease after acute kidney injury: a systematic review and meta-analysis," Kidney Int, 2012, 81:442-448.

Constantin et al., "Plasma neutrophil gelatinase-associated lipocalin is an early marker of acute kidney injury in adult critically ill patients: a prospective study," J Crit Care, 2010, 25:176.e1-176.e6.

Cwirla et al., "Peptides on phage: A vast library of peptides for identifying ligands," Proc Natl Arad Sci USA, Aug. 1990, 87:6378-6382.

Devarajan, "Update on Mechanisms of Ischemic Acute Kidney Injury," J Am Soc Nephrol, 2006, 17:1503-1520.

Devarajan, "Emerging Biomarkers of Acute Kidney Injury," Contrib Nephrol, 2007, 156:203-212.

Devlin et al., "Random Peptide Libraries: A Source of Specific Protein Binding Molecules," Science, Jul. 27, 1990, 249:404-406.

Dirks et al., "Effect of saline infusions and furosemide on the dog distal nephron," Am J Physiol, Jul. 1970, 219(1):114-121.

Doi et al., "Urinary L-type fatty acid-binding protein as a new renal biomarker in critical care," Curr Opin Crit Care, 2010, 16:545-549.

Fischer et al., "A readers' guide to the interpretation of diagnostic test properties: clinical example of sepsis," Intensive Care Med, 2003, 29:1043-1051.

Forrey et al., "Furosemide Concentrations in Serum and Urine, and its Binding by Serum Proteins as Measured Fluorometrically," Clin Chem, 1974, 20(2):152-158.

Gibney et al., "Timing of Initiation and Discontinuation of Renal Replacement Therapy in AKI: Unanswered Key Questions," Clin J Am Soc Nephrol, 2008, 3:876-880.

Goldstein et al., "Renal Angina," Clin J Am Soc Nephrol, 2010, 5:943-949.

Hall et al., "Risk of Poor Outcomes with Novel and Traditional Biomarkers at Clinical AKI Diagnosis," Clin J Am Soc Nephrol, 2011, 6:2740-2749, plus Supplemental Data, 13 pp total.

Hasannejad et al., "Interactions of Human Organic Anion Transporters with Diuretics," J Pharmacol Exp Ther, 2004, 308:1021-1029.

Heyman et al., "Loop diuretics reduce hypoxic damage to proximal tubules of the isolated pertused rat kidney," Kidney Int, 1994, 45:981-985.

Ho et al., "Benefits and risks of furosemide in acute kidney injury," Anaesthesia, 2010, 65:283-293.

Hsu et al., "Temporal Changes in Incidence of Dialysis-Requiring AKI," J Am Soc Nephrol, 2013, 24:37-42, plus Supplemental Data, 8 pp total.

Kellum, "Acute kidney injury," Crit Care Med, 2008, 36(4)(Suppl):S141-S145.

Knaus et al., "Apache II: A severity of disease classification system," Crit Care Med, 1985, 13(10):818-829.

Koyner et al., "Use of stress tests in evaluating kidney disease," Current Opinion in Nephrology and Hypertension, 2017, 26(1):31-35.

Koyner et al., "Urinary Biomarkers in the Clinical Prognosis and Early Detection of Acute Kidney Injury," Clin J Am Soc Nephrol, 2010, 5:2154-2165.

Koyner et al., "Biomarkers Predict Progression of Acute Kidney Injury after Cardiac Surgery," J Am Soc Nephrol, 2012, 23:905-914, plus Supplemental Data, 15 pp total.

Lassnigg et al., Minimal Changes of Serum Creatinine Predict Prognosis in Patients after Cardiothoracic Surgery: A Prospective Cohort Study, J Am Soc Nephrol, 2004, 15:1597-1605.

Levey et al., "A More Accurate Method To Estimate Glomerular Filtration Rate from Serum Creatinine: A New Prediction Equation," Modification of Diet in Renal Disease Study Group, Ann Intern Med, Mar. 16, 1999, 130(6):461-470.

Loon et al., "Mechanism of impaired natriuretic response to furosemide during prolonged therapy," Kidney Int, 1989, 36:682-689.

McCullough et al., "Contrast-Induced Nephropathy (CIN) Consensus Working Panel: Executive Summary," Rev Cardiovasc Med, 2006, 7(4):177-197.

Mehran et al., "A Simple Risk Score for Prediction of Contrast-Induced Nephropathy After Percutaneous Coronary Intervention: Development and Initial Validation," J Am Col Cardiol, 2004, 44(7):1393-1399.

Mehta et al., "Diuretics, Mortality, and Nonrecovery of Renal Function in Acute Renal Failure," JAMA, Nov. 27, 2002, 288(20):2547-2553.

Mehta et al., "Acute Kidney Injury Network: report of an initiative to improve outcomes in acute kidney injury," Crit Care, 2007, 11:R31, 8 pp.

Nelson et al., "A computer program for calculating antibody affinity constants," Comput Methods Programs Biomed, 1988, 27:65-68.

Otero et al., "A Device for Automatically Measuring and Supervising the Critical Care Patient's Urine Output," Sensors, 2010, 10:934-951.

Panagiotou et al., "Continuous Real-Time Urine Output Monitoring for Early Detection of Acute Kidney Injury," Contrib Nephrol, 2011, 171:194-200.

Pandit et al., "Response to furosemide as a marker of acute kidney injury in post-operative CABG patients," J Am Coll Surg, Sep. 2011, 213(3)(Suppl):S46.

Praught et al., "Are small changes in serum creatinine an important risk factor?," Curr Opin Nephrol Hypertens, 2005, 14:265-270.

Ricci et al., "The RIFLE criteria and mortality in acute kidney injury: A systematic review," Kidney Int, 2008, 73:538-546.

(56) References Cited

OTHER PUBLICATIONS

Scott et al., "Searching for Peptide Ligands with an Epitope Library," Science, 1990, 249:386-388.
Seabra et al., "Timing of Renal Replacement Therapy Initiation in Acute Renal Failure: A Meta-analysis," Am J Kidney Dis, 2008, 52:272-284.
Thakar et al., "A Clinical Score to Predict Acute Renal Failure after Cardiac Surgery," J Am Soc Nephrol, 2005, 16:162-168.
Van Erp et al., "Application of a Sol Particle Immunoassay to the Determination of Affinity Constants of Monoclonal Antibodies," J Immunoassay, 1991, 12(3):425-443.
Vincent et al., "The SOFA (Sepsis-related Organ Failure Assessment) score to describe organ dysfunction/failure," Intensive Care Med, 1996, 22:707-710.
Ward et al., Binding activities of a repertoire of single immunoglobulin variable domains secreted from *Escherichia coli,* Nature, Oct. 12, 1989, 341:544-546.
Wijeysundera et al., "Derivation and Validation of a Simplified Predictive Index for Renal Replacement Therapy After Cardiac Surgery," JAMA,.Apr. 25, 2007, 297:1801-1809.
Wilson et al., "Simplified conjugation chemistry for coupling peptides to F(ab') fragments: autologous red cell agglutination assay for HIV-1 antibodies," J Immunol Methods, 1994, 175:267-273.
Yarmush et al., "Coupling of antibody-binding fragments to solid-phase supports: site-directed binding of F(ab')2 fragments," J Biochem Biophys Methods, 1992, 25:285-297.
Office Action issued Sep. 13, 2017 in Chinese application 201480044695.1, including English translation.
Office Action issued Jul. 30, 2019 in European application 14806904.0.
Office Action issued May 18, 2020 in European application 14806904.0.
Extended European Search Report and Written Opinion issued May 4, 2017 in European application 14806904.
Partial European Search Report issued Jan. 2, 2017 in European application 14806904.0.
International Search Report and Written Opinion issued Oct. 27, 2014 in PCT/US2014/041156 (10 pages).
Herget-Rosenthal et al., "Early detection of acute renal failure by serum cystatin C," Kidney Int, 2004, 66(3):1115-1122.
Sakhuja et al., "Role of Loop Diuretic Challenge in Stage III Acute Kidney Injury," Mayo Clin Proc, Aug. 2019, 94(8):1509-1515.
Office Action issued Oct. 5, 2021 in European application No. 14806904.0.
International Preliminary Report on Patentability received for PCT Patent Application No. PCT/US14/41156, mailed on Dec. 17, 2015, 8 pages.

* cited by examiner

METHODS AND COMPOSITIONS FOR DIAGNOSIS AND PROGNOSIS OF RENAL INJURY AND RENAL FAILURE

The present application claims priority to U.S. Provisional Patent Application No. 61/831,294, filed Jun. 5, 2013, and to U.S. Provisional Patent Application No. 61/862,913, filed Aug. 6, 2013, each of which is hereby incorporated in its entirety.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, 17$^{th}$ Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, 47$^{th}$ Ed, McGraw Hill, New York pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, 17$^{th}$ ed., Chapter 222, and which is hereby incorporated by reference in their entirety:

| Type | Risk Factors |
|---|---|
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48 h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, *Curr Opin Nephrol Hypertens* 14:265-270, 2005 and Chertow et al, *J Am Soc Nephrol* 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, J Am Soc Nephrol 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., *Crit Care.* 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;
"Injury": serum creatinine increased 2.0 fold from baseline OR urine production <0.5 ml/kg/hr for 12 h;
"Failure": serum creatinine increased 3.0 fold from baseline OR creatinine >355 μmol/l (with a rise of >44) or urine output below 0.3 ml/kg/hr for 24 h or anuria for at least 12 hours;
And included two clinical outcomes:
"Loss": persistent need for renal replacement therapy for more than four weeks.
"ESRD": end stage renal disease—the need for dialysis for more than 3 months.

These criteria are called the RIFLE criteria, which provide a useful clinical tool to classify renal status. As discussed in Kellum, *Crit. Care Med.* 36: S141-45, 2008 and Ricci et al., *Kidney Int.* 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients, which have been modified from RIFLE:
"Stage I": increase in serum creatinine of more than or equal to 0.3 mg/dL (≥26.4 μmol/L) or increase to more than or equal to 150% (1.5-fold) from baseline OR urine output less than 0.5 mL/kg per hour for more than 6 hours;
"Stage II": increase in serum creatinine to more than 200% (>2-fold) from baseline OR urine output less than 0.5 mL/kg per hour for more than 12 hours;
"Stage III": increase in serum creatinine to more than 300% (>3-fold) from baseline OR serum creatinine ≥354 μmol/L accompanied by an acute increase of at least 44 μmol/L OR urine output less than 0.3 mL/kg per hour for 24 hours or anuria for 12 hours.

The CIN Consensus Working Panel (McCollough et al, Rev Cardiovasc Med. 2006; 7(4):177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Although serial measurement of serum creatinine over a period of days is an accepted method of detecting and diagnosing AKI and is considered one of the most important tools to evaluate AKI patients, serum creatinine is generally regarded to have several limitations in the diagnosis, assessment and monitoring of AKI patients. The time period for serum creatinine to rise to values (e.g., a 0.3 mg/dL or 25% rise) considered diagnostic for AKI can be 48 hours or longer depending on the definition used. Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Some patients with AKI will recover fully, some will need dialysis (either short term or long term) and some will have other detrimental outcomes including death, major adverse cardiac events and chronic kidney disease. Because serum creatinine is a marker of filtration rate, it does not differentiate between the causes of AKI (pre-renal, intrinsic renal, post-renal obstruction, atheroembolic, etc) or the category or location of injury in intrinsic renal disease (for example, tubular, glomerular or interstitial in origin). Urine output is similarly limited, Knowing these things can be of vital importance in managing and treating patients with AKI.

These limitations underscore the need for better methods to detect and assess AKI, particularly in the early and subclinical stages, but also in later stages when recovery and repair of the kidney can occur. Furthermore, there is a need to better identify patients who are at risk of having an AKI.

BRIEF SUMMARY OF THE INVENTION

It is an object of the present invention to provide a combination of a functional assessment of renal function together with biomarker results in order to improve assessment of patient at risk of, or having, an acute kidney injury. A loop diuretic such as furosemide inhibits luminal active chloride transport throughout the thick ascending limb of Henle, thereby preventing sodium reabsorption and resulting in natriuresis and increased urine flow. Loop diuretic-induced increases in urine output might be a method to assess the integrity of the renal tubular function in the setting of early AKI, and so a kidney's response, or lack thereof, to a diuretic challenge as a clinical assessment of tubular function can identify patients with severe tubular injury before it is clinically apparent (e.g. a rise in creatinine).

However, because administration of loop diuretics is, by definition, an interventional procedure having the potential for undesirable systemic effects, the present invention relies on an initial biomarker assay on a body fluid sample obtained from the patient to provide an initial assessment of the risk of acute kidney injury for the patient. By correlating the biomarker assay result to the patient's risk of acute kidney injury, the patient's suitability for receiving the diuresis stress evaluation is determined; in effect, if the patient's biomarker results indicate a substantial risk of acute kidney injury, the need for the follow-up diuresis stress evaluation is diminished, and the patient may be treated based on the risk indicated from the biomarker result. If the biomarker results indicate a reduced risk, the diuresis stress evaluation can provide additional risk information to the clinician.

Thus, in a first aspect, the present invention relates to a method of evaluating a patient for acute kidney injury progression, comprising:
  performing a biomarker assay on a body fluid sample obtained from the patient to provide an assay result, wherein the biomarker(s) in the biomarker assay are correlated to a risk of acute kidney injury;
  correlating the assay result to the patient's risk of acute kidney injury relative to a risk in a predetermined population of individuals;
  classifying the patient's suitability for receiving a diuresis stress evaluation using the patient's risk of acute kidney injury;
  if the patient is classified as suitable, performing the diuresis stress evaluation on the patient to provide a furosemide-induced urine output value; and
  correlating the diuresis-induced urine output value to a risk of acute kidney injury progression.

Biomarkers suitable for the biomarker assay component of the present invention include, but are not limited to, one or more biomarkers selected from the group consisting of Metalloproteinase inhibitor 2, Thrombospondin-1, Antileukoproteinase, Insulin-like growth factor-binding protein 7, Metalloproteinase inhibitor 4, Metalloproteinase inhibitor 1, Hyaluronic acid, Transmembrane glycoprotein NMB, Follistatin, Hepatocyte growth factor, Tumor necrosis factor receptor superfamily member 6, Growth-regulated alpha protein, C-C motif chemokine 24, Metalloproteinase inhibitor 3, C-X-C motif chemokine 6, Tumor necrosis factor receptor superfamily member 11B, Cystatin-C, Beta-2-microglobulin, Serum albumin, Clusterin, Interleukin-8, Neutrophil gelatinase-associated lipocalin, Interleukin-2 receptor alpha chain, Hepatitis A virus cellular receptor 1, Chitinase-3-like protein 1, Serum creatinine, and Hyaluronic acid. This list is not meant to be limiting. In preferred embodiments, the biomarker assay component of the present invention can comprise measuring the concentration of Metalloproteinase inhibitor 2 and/or Insulin-like growth factor-binding protein 7.

In addition to biomarker results, additional clinical indicia of health status, and particularly of renal sufficiency, may be included in the method for classifying the patient's suitability for receiving a diuresis stress evaluation. Such clinical indicia may include one or more of: a baseline urine output value for the patient, a baseline change in serum creatinine for the patient, demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), other clinical variables (e.g., blood pressure, temperature, respiration rate), risk scores (APACHE score, PREDICT score, TIMI Risk Score for UA/NSTEMI, Framingham Risk Score, risk scores of Thakar et al. (J. Am. Soc. Nephrol. 16: 162-68, 2005), Mehran et al. (J. Am. Coll. Cardiol. 44: 1393-99, 2004), Wijeysundera et al. (JAMA 297: 1801-9, 2007), Goldstein and Chawla (Clin. J. Am. Soc. Nephrol. 5: 943-49, 2010), or Chawla et al. (Kidney Intl. 68: 2274-80, 2005)), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatinine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more kidney injury marker assay result(s) are described hereinafter and in Harrison's Principles of Internal Medicine, 17th Ed., McGraw Hill, New York, pages 1741-1830, and Current Medical Diagnosis & Treatment 2008, 47th Ed, McGraw Hill, New York, pages 785-815, each of which are hereby incorporated by reference in their entirety. By way of example only, the method for classifying the patient's suitability for receiving a diuresis stress evaluation may comprise determining if the patient has experienced 6 hours of oliguria defined as a urine output of <0.5 ml/kg/hour, or a 0.3 mg/dL rise in serum creatinine, or an increase of 150-200% above a baseline serum creatinine concentration.

Various methods may be used to evaluate the biomarker results in order to classify the patient as suitable or unsuitable to receive a diuresis stress evaluation. By way of example, a cutoff for a biomarker may be selected which has been predetermined to divide a relevant population into two or more groups. A first group, often called the "nondiseased" population for convenience, represents those patients which have a high risk of AKI, and so the diuresis stress evaluation is not indicated. A second group represents those patients with a risk of AKI is small as measured by the biomarker result, but for whom the diuresis stress evaluation may be performed to improve patient management. A relative risk of AKI for the second group is determined relative to the risk in the first group. A relative risk of 1 means there is no difference in risk between the two groups; while a relative risk of >1 means the risk is higher in the second group. In certain embodiments, the patient is identified as suitable to receive the diuresis stress evaluation if the relative risk is greater than 1; is about 1.5 or greater; is about 2 or greater; is about 3 or greater; or is about 5 or greater. In other embodiments, the patient is identified as unsuitable to receive the diuresis stress evaluation if the relative risk is 1 or less; is less than about 1.5; is less than about 2; is less than about 3; or is less than about 5. Preferably, the classifying step comprises identifying the patient as suitable to receive a diuresis stress evaluation if the patient is not suffering from an existing acute kidney injury.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more kidney injury markers, or a composite of such markers, may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1-specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

In certain embodiments, the subject is selected for risk stratification based on the pre-existence in the subject of one or more known risk factors for prerenal, intrinsic renal, or postrenal ARF. For example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin are all preferred subjects for monitoring risks according to the methods described herein.

Loop diuretics are diuretics that act on the ascending loop of Henle in the kidney, as opposed to thiazide diuretics which inhibit reabsorption of sodium (Na+) and chloride (Cl—) ions from the distal convoluted tubules in the kidneys. Loop diuretics which may find use in the methods of the present invention include, but are not limited to, Bumetanide, Ethacrynic acid (Edecrin), Furosemide (Lasix), and Torsemide (Demadex). This list is not meant to be limiting. By way of example, the diuresis stress evaluation of the present invention comprises (ii) determining a baseline urine output value for the patient prior to intravenous administration of a loop diuretic such as furosemide, (ii) administering the diuretic (furosemide) intravenously to the patient in an amount effective to cause diuresis, (ii) and determining the diuretic-induced urine output value. As in the case of the biomarker results, correlating the diuretic-induced urine output value to a risk of acute kidney injury progression may be performed in a variety of manners, such as comparing the diuretic-induced urine output value to a cutoff value, wherein the cutoff value identifies patients that will progress to acute kidney failure with a sensitivity of at least 50% and a specificity of at least 50%. In certain embodiments, the cutoff value identifies patients that will progress to acute kidney failure with a sensitivity of at least 75% and a specificity of at least 75%.

In addition to, or as an alternative to, the use of loop diuretics, one or more diuretics selected from the group consisting of mannitol, furosemide, bumetanide, ethacrynic acid, torsemidehydrochlorothiazide, bendroflumethiazide, hydroflumethiazide, chlorothiazide, polythiazide, trichlormethiazide, cyclopenthiazide, methyclothiazide, cyclothiazide, and mebutizide or their equivalents may be used in performing the diuresis stress evaluation of the present invention. This list is not meant to be limiting.

In certain embodiments, preferably the likelihood or risk assigned is that an event of interest is more or less likely to occur within 180 days of the time at which the diuresis stress evaluation is performed. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the diuresis stress evaluation is performed is equivalent to diagnosis of a current condition.

In certain embodiments, fluid is administered to the patient intravenously to balance the diuresis-induced urine output. Management of intravenous fluid replacement is a key aspect of the treatment of kidney injury and heart failure. Although volume resuscitation may be needed to restore cardiac output, it often leads to tissue edema and organ dysfunction. However, hypovolemia and renal hypoperfusion can occur in patients with AKI if excessive fluid removal is pursued with diuretics or extracorporeal therapy. Thus, the present invention can utilize various means for accurate assessment of fluid status during the diuresis stress evaluation. By way of example, a diuresis-induced urine output value may be measured continuously during the evaluation. Sensor devices for continuous real-time urine output monitoring are known in the art. See, e.g., Panagiotou et al., Contrib. Nephrol. 171: 194-200, 2011; Otero et al, Sensors 10: 934-51, 2010; US 20100121220.

In certain embodiments, the fluid which is lost to diuresis as urine may be compensated by fluid administration, e.g. as intravenous saline. Albumin is the main determinant of plasma osmotic pressure, so in certain embodiments albumin may be included in the replacement fluid. For example, serum albumin may be maintained at approximately 20 g/L.

In preferred embodiments, the diuresis-induced urine output value may be determined by such a sensor that is operably connected to a controller comprising a microprocessor which receives an electronic signal from the sensor and calculates the diuresis-induced urine output value from the sensor signal. Such a controller may be further operably connected to a fluid infusion system. In this system, the diuresis-induced urine output value calculated by the microprocessor may be used to control delivery of fluid to the patient by the fluid infusion system to balance the diuresis-induced urine output in an automated fashion in order to optimize fluid replacement management.

In certain embodiments, the methods of the present invention can further comprise measuring an amount of the diuretic administered in the diuresis stress evaluation which appears in the urine. Certain patients can be referred to as being "diuretic resistant." Diuretic resistance may be caused by decreased renal function and reduced and delayed peak concentrations of loop diuretics in the tubular fluid, but it can also be observed in the absence of these pharmacokinetic abnormalities. The amount of diuretic appearing in the urine, together with the amount of urine produced in response to diuresis, can be used to determine of the patient is suffering from a pre-renal kidney injury or an acute tubular kidney injury. The ability to identify the type of injury can be key to guiding therapy. Prerenal failure is often indicative of advanced heart disease with very low cardiac output, extracellular volume depletion, or acute blood loss. In contrast, acute tubular injury is often indicative of administration of nephrotoxic drugs, radiographic contrast media, and acute glomerulonephritis. Systemic sepsis may result in either prerenal or acute tubular injury.

DETAILED DESCRIPTION OF THE INVENTION

Acute kidney injury (AKI) is a clinical syndrome that is associated with significant morbidity and mortality. The incidence of AKI has more than doubled in the past decade and is projected to continue to increase. Patients with AKI are cared for by a multitude of specialists including, but not limited to, emergency medicine physicians, internists, pediatricians, surgeons, intensivists, and nephrologists. Patients who develop AKI often require renal replacement therapy (RRT), but clinicians often disagree about the optimal timing of the initiation of RRT. During the Acute Kidney Injury Network (AKIN) multi-disciplinary consensus meeting, the question that was ranked highest was "When should RRT be initiated?" RRT is an invasive procedure with inherent risks, and one would not want to initiate this therapy if the patient were destined to recover renal function without intervention. However, a more conservative approach of initiating RRT late in the course of the AKI can subject the patient to adverse consequences. Thus, if a test could be devised that predicts the likelihood of progressing to more severe stage of AKI, decisions regarding optimal timing of RRT initiation would be better informed.

Because serum creatinine and oliguria are often late signs of significant AKI, more sensitive diagnostic tests are required. This clinical need has led to the development of multiple candidate AKI biomarkers. Because AKI biomarker levels change over time depending on the timing and severity of injury, a functional assessment of renal function may enhance biomarker performance. Furosemide, a loop diuretic, has pharmacokinetic properties that make it an appealing functional tool. As an organic acid, furosemide is tightly bound to serum proteins and gains access to the tubular lumen by active secretion via the human organic anion transporter (hOAT) system in the proximal convoluted tubule. Once in the tubular lumen, furosemide inhibits luminal active chloride transport throughout the thick ascending limb of Henle, thereby preventing sodium reabsorption and resulting in natriuresis and increased urine flow. Furosemide induced increases in urine output, combined with biomarker assays, provide a method to assess the integrity of the renal tubular function before it was clinically apparent through a rise in creatinine.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL ($\geq$8.8 µmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl ($\geq$26.4 µmol/l), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

Loop Diuretics

Loop diuretics are diuretics that act on the ascending loop of Henle in the kidney. They are primarily used in medicine to treat hypertension and edema often due to congestive heart failure or renal insufficiency. While thiazide diuretics are more effective in patients with normal kidney function, loop diuretics are more effective in patients with impaired kidney function.

Examples of loop diuretics for use in the present invention include, but are not limited to, Furosemide, Bumetanide, Ethacrynic acid, and Torsemide. Appropriate dosages to achieve diuresis using such loop diuretics are known to those of skill in the art. By way of example, suitable dosages may be 40 to 80 mg of furosemide, 2 to 3 mg of bumetanide, or 20 to 50 mg of torsemide administered intravenously (either by bolus or continuous infusion over time). Renal insufficiency causes decreased bloodflow to the kidneys, which decreases the glomerular filtration rate (GFR) and reduces the ability of loop diuretics to reach their target organ, the loop of Henle. In patients with reduced GFR, appropriate dosages of loop diuretics for use in the present invention may be increased proportionally to the decrease in GFR. Dosages may also be increased for oral furosemide, since its bioavailability is only about 50 percent as compared to intravenous administration. In severe renal insufficiency, dosages as high as 200 mg of furosemide, 8 to 10 mg of bumetanide, or 50 to 100 mg of torsemide may be employed.

A diuretic stress evaluation is performed by administration of the desired diuretic, followed by measurement of urine output. By way of example, urine output may be measured every thirty minutes or hourly for six hours and/or in total for 6, 8, 12, or 24 hours. This is not meant to be limiting. Other features of the urine related to diuretic use, such as urinary sodium, urinary potassium, urine osmolarity, etc., may also be evaluated. The result may be expressed as a maximal urine flow rate, or as a total urine volume over time. In certain embodiments, the result is compared to a measurement of the same variable prior to the administration of the diuretic.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like. Such instruments may, in general, be designed to assay all or a portion of a sample introduced into the instrument for the analyte(s) of interest by, for example, causing all or a portion of a sample to be contacted with a specific binding agent for each analyte of interest and detecting bound complexes of the analyte with its corresponding binding agent. Other formats are known in the art.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dinitrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CHl domains; (ii) a F(ab')2 fragment, a bivalent fragment comprising two Fab fragments linked by a disulfide bridge at the hinge region; (iii) a Fd fragment consisting of the VH and CHl domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ $M^{-1}$, and preferably between about $10^8$ $M^{-1}$ to about $10^9 M^{-1}$, about $10^9 M^{-1}$ to about $10^{10}$ $M^{-1}$, or about $10^{10}$ $M^{-1}$ to about $10^{12}$ $M^{-1}$.

Affinity is calculated as $K_d=k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c=K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

While the present application describes antibody-based binding assays in detail, alternatives to antibodies as binding species in assays are well known in the art. These include receptors for a particular target, aptamers, etc. Aptamers are oligonucleic acid or peptide molecules that bind to a specific target molecule. Aptamers are usually created by selecting them from a large random sequence pool, but natural aptamers also exist. High-affinity aptamers containing modified nucleotides conferring improved characteristics on the ligand, such as improved in vivo stability or improved delivery characteristics. Examples of such modifications include chemical substitutions at the ribose and/or phosphate and/or base positions, and may include amino acid side chain functionalities.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the 97.5th percentile of the concentration seen in a normal population. Another method may be to look at serial samples from the same patient, where a prior "baseline" result is used to monitor for temporal changes in a biomarker level.

Population studies may also be used to select a decision threshold. Receiver Operating Characteristic ("ROC") arose from the field of signal detection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1−specificity, the ROC graph is sometimes called the sensitivity vs (1−specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1−specificity)) of greater than 1, at least 2, more preferably at least 3, still more preferably at least 5, and most preferably at least 10; and or a negative likelihood ratio (calculated as (1−sensitivity)/specificity) of less than 1, less than or equal to 0.5, more preferably less than or equal to 0.3, and most preferably less than or equal to 0.1

Biomarkers and clinical indicia may be combined with the loop diuretic stress evaluation according to the present invention. Examples of biomarkers related to renal status include the following

| | |
|---|---|
| Metalloproteinase inhibitor 2 | P16035 |
| Thrombospondin-1 | P07996 |
| Antileukoproteinase | P03973 |
| Insulin-like growth factor-binding protein 7 | Q16270 |
| Metalloproteinase inhibitor 4 | Q99727 |
| Metalloproteinase inhibitor 1 | P01033 |
| Hyaluronic acid | AST-HA |
| Transmembrane glycoprotein NMB | Q14956 |
| Follistatin | P19883 |
| Hepatocyte growth factor | P14210 |

-continued

| Tumor necrosis factor receptor superfamily member 6 | P25445 |
| Growth-regulated alpha protein | P09341 |
| C-C motif chemokine 24 | O00175 |
| Metalloproteinase inhibitor 3 | P35625 |
| C-X-C motif chemokine 6 | P80162 |
| Tumor necrosis factor receptor superfamily member 11B | O00300 |
| Cystatin-C | P01034 |
| Beta-2-microglobulin | P61769 |
| Serum albumin | P02768 |
| Clusterin | P10909 |
| Interleukin-8 | P10145 |
| Neutrophil gelatinase-associated lipocalin | P80188 |
| Interleukin-2 receptor alpha chain | P01589 |
| Hepatitis A virus cellular receptor 1 | Q96D42 |
| Chitinase-3-like protein 1 | P36222 |
| Serum creatinine | n/a |
| Hyaluronic acid | n/a |

Clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatinine ratio, and/or a renal failure index calculated as urine sodium/(urine creatinine/plasma creatinine). Other measures of renal function which may be combined in the methods of the present invention are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

Combining assay results/clinical indicia in this manner can comprise the use of multivariate logistical regression, log linear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 m$^2$ can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr-corrected} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., *Nephrol. Dial. Transplant.* 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, NJ, 1999. In addition, since the methods and compositions described herein provide prognostic information, the markers of the present invention may be used to monitor a course of treatment. For example, improved or worsened prognostic state may indicate that a particular treatment is or is not efficacious.

The distinction between prerenal AKI and intrinsic AKI is an important clinical assessment that directs the therapeutic intervention(s). Patients who are prerenal need therapies directed at hemodynamics to improve renal blood flow. These therapies are often involve inotropes, intravenous fluids and/or vasopressors. Each of these interventions have potential side effects (e.g. arrhythmias, volume overload, vasoconstriction) and would not be advisable to implement these therapies if they are not destined to improve renal function. Thus, the distinction between prerenal AKI and intrinsic AKI helps determine the therapy which should be prescribed. If prerenal AKI is not present, therapy is directed at mitigating AKI and providing supportive care.

Prerenal acute renal failure occurs when a sudden reduction in blood flow to the kidney camera (renal hypoperfusion) causes a loss of kidney function. Causes can include low blood volume, low blood pressure, shunting of blood from the kidney, heart failure, and local changes to the blood vessels supplying the kidney. In prerenal acute renal failure, there is nothing wrong with the kidney itself. Treatment focuses on correcting the cause of the prerenal acute renal failure.

In prerenal AKI without fluid overload, administration of intravenous fluids is typically the first step to improve renal function. This is particularly used in patients in whom prerenal AKI develops as the result of intravascular volume depletion in order to restore normal circulating blood volume. Volume status may be monitored to avoid over- or under-replacement of fluid as described herein. Fluids with colloidal particles such as albumin may be preferred over simple saline infusion. In a prerenal condition wherein the forward flow is compromised, drugs directed at augmenting cardiac output are typically employed.

In patients with congestive heart failure in whom AKI has developed as a result of excessive diuresis, withholding of diuretics and cautious volume replacement may be sufficient to restore kidney function. Inotropes such as norepinephrine and dobutamine may be given to improve cardiac output and hence renal perfusion.

Hospitalized fluid overload patients are typically treated with fluid restriction, IV diuretics, inotropes (e.g., milrinone or dobutamine) and combination therapies. The loop diuretic furosemide is the most frequently prescribed diuretic for treatment of volume overload in HF. Initial oral doses of 20 to 40 mg once a day should be administered to patients with dyspnea on exertion and signs of volume overload who do not have indications for acute hospitalization. Severe overload and pulmonary edema are indications for hospitalization and intravenous furosemide. Some patients with mild HF can be treated effectively with thiazide diuretics. Those who have persistent volume overload on a thiazide diuretic should be switched to an oral loop diuretic. In patients with severe kidney injury, diuretics may not result in significant diuresis. Ultrafiltration, also called aquapheresis, may be used to treat fluid overload in such cases.

In contrast to prerenal AKI, the main goal of treatment of acute tubular necrosis (ATN) is to prevent further injury to the kidney. Ischemic ATN can be caused when the kidneys are not sufficiently perfused for a long period of time (e.g. due to renal artery stenosis) or by shock. Sepsis causes 30% to 70% of deaths in patients with ATN; therefore, avoidance of intravenous lines, bladder catheters, and respirators is recommended. Because septic patients are vasodilated, large volumes of administered fluid accumulate in the lung interstitium of these patients. Extracellular fluid volume should be assessed promptly, and repletion of any deficit should be initiated promptly. Hemodynamic status should be modified by appropriate fluid therapy, giving vasopressors and/or inotropes and treating any underlying sepsis. All possible nephrotoxic drugs should be stopped. In addition, doses of all medications that are eliminated by the kidney should be adjusted.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1

The following study was performed on two separate cohorts of critically ill patients with either stage I or II Acute Kidney Injury Network (AKIN) criteria (Table A) who were given a standardized dose of furosemide and assessed their response and outcomes.

Cohort 1 (Test)

The Southern Acute Kidney Injury Network (SAKInet) was formed in 2007 to collect samples from patients who developed AKI with the goal of testing the diagnostic and prognostic accuracy of previously described and novel AKI biomarkers. We identified a subset of patients from the SAKInet cohort at the George Washington University who fulfilled the study criteria.

Cohort 2 (Validation)

The protocol for cohort 2 was registered in clinicaltrials.gov. The study was carried out at the George Washington University (NCT00673244) and at the University of Chicago (NCT01275729). The respective university IRBs approved the identical protocol. Patients or their surrogates were required to sign informed consent prior to study entry. Patients were enrolled from June 2009 through December 2012. Urine sediment was assessed with the George Washington Urine Sediment Score (GW USS) as described previously.

Study Criteria (Both Cohorts 1 and 2)

Inclusion Criteria: (1) age greater than 18 admitted in an ICU, (2) AKIN stage I (6 hours of oliguria [<0.5 ml/kg/hour] or 0.3 mg/dL rise in serum creatinine, or, increase in 150-200% above baseline serum creatinine) OR, AKIN stage II (12 hours of oliguria [<0.5 ml/kg/hour] or increase in 200-300% above baseline serum creatinine) (3) indwelling bladder catheter (4) presence of granular or epithelial cell casts on urine sediment [defined by GW USS≥2] or a fractional excretion of sodium (FeNa)>1.0%, (5) treating clinical team deemed the patient to be well-resuscitated.

Exclusion Criteria: (1) Baseline eGFR<30 ml/min/1.73 m$^2$, (2) history of renal allograft, (3) known pregnancy, (4) evidence of obstructive uropathy [e.g. hydroureter], (5) evidence of active bleeding, (6) patients with allergy or known sensitivity to loop diuretics, (7) achievement of AKIN stage III criteria, or (8) evidence of volume depletion at the time of furosemide administration.

Study Procedures (Cohort 1)

Patients in the SAKInet cohort who met the study criteria, and who received a furosemide dose of 1.0 mg/kg were entered into Cohort 1. Replacement fluid was not protocolized in this group of subjects. Demographic, clinical data, urine sediment scores, and outcome data were abstracted from the case report forms.

Study Procedures (Cohort 2):

Prior to FST urine was collected. A pre-FST FeNa was only available if the treating team had ordered one for clinical purposes. After acquisition of informed consent, patients who were loop diuretic naïve were given 1.0 mg/kg of intravenous furosemide. Since patients who were previously treated with loop diuretics within the previous 7 days were likely to have a blunted response over time compared to naïve patients, this group received an intravenous dose of 1.5 mg/kg. (As little as 6-8 days of chronic loop diuretic therapy is associated with a blunted response to furosemide due to increased distal tubular uptake of sodium in the thiazide sensitive nephron segment). In order to minimize the risk of hypovolemia, urine output was replaced ml for ml each hour with either Ringers lactate or normal saline for six hours after the FST. The treating team could elect not to replace the volume if net volume loss was considered clinically desirable.

Urine output was measured hourly for six hours and in total for 24 hours. Any and all adverse events related to furosemide were recorded including, but not limited to, tinnitus, hypokalemia, hypomagnesemia and hypotension. Patients were followed for 14 days or hospital discharge, whichever occurred first. Fractional excretion of sodium was calculated as described in Bagshaw and colleagues. MDRD equation was used to calculate the eGFR as described in Levey and colleagues. Cardiovascular SOFA score and APACHE II score were calculated as previously described.

TABLE 1

Patient Characteristics Between Cohorts

| Variable | Combined n = 77 | Cohort 1 n = 23 | Cohort 2 n = 54 | p |
|---|---|---|---|---|
| Age (years, s.e.) | 65.3 (1.6) | 70.0 (2.5) | 63.1 (2.0) | 0.03 |
| Male (n, %) | 33 (42.8%) | 11 (47.8%) | 22 (40.7%) | 0.62 |
| Race | | | | |
| African American | 44 (57.1%) | 12 (52.2%) | 32 (59.3%) | 0.57 |
| Caucasian | 23 (29.9%) | 7 (30.4%) | 16 (29.6%) | 0.90 |
| Hispanic | 10 (13.0%) | 4 (17.4%) | 6 (11.1%) | 1.00 |
| Comorbidites n (%) | | | | |
| CKD | 24 (31%) | 6 (26.1%) | 18 (33.3%) | 0.60 |
| Hypertension | 60 (78%) | 19 (82.6%) | 41 (75.9%) | 0.77 |
| CHF | 25 (33%) | 8 (34.8%) | 17 (31.5%) | 0.49 |
| DM | 35 (44%) | 11 (4.8%) | 24 (44.4%) | 0.49 |
| Nephrotoxic Exposures | | | | |
| NSAIDS | 8 (10)% | 0 (0%) | 8 (14.8%) | 0.10 |
| Aminoglycosides | 1 (1%) | 0 (0%) | 1 (1.9%) | 1.00 |
| Amphotericin | 2 (3%) | 0 (0%) | 2 (3.7%) | 1.00 |
| Contrast | 21 (27%) | 7 (30.4%) | 14 (25.9%) | 0.78 |
| Post-cardiac surgery | 9 (11.7%) | 0 (0%) | 9 (16.7%) | 0.05 |
| Sepsis | 15 (19.5%) | 0 (0%) | 15 (27.8%) | 0.01 |
| Clinical Data | | | | |
| Baseline eGFR (ml/min/1.73 m$^2$) | 68.6 (4.1) | 58 (9.7) | 73.2 (4.0) | 0.16 |
| Furosemide Naive | 29 (37.7%) | 8 (34.8%) | 21 (38.9%) | 0.80 |
| Urine Cast Score | 2.3 (.13) | 2.2 (0.27) | 2.4 (0.15) | 0.57 |
| FeNa (above 1%)* | 14 (18%) | 4 (17.4%) | 10 (18.5%) | 0.91 |
| CV SOFA Score | 1.16 (0.3) | 1.9 (0.29) | 1.18 (0.19) | 0.04 |
| APACHE II Score | 17.8 (1.11) | 21.3 (1.7) | 17.8 (1.1) | 0.09 |

TABLE 1-continued

Patient Characteristics Between Cohorts

| Variable | Combined n = 77 | Cohort 1 n = 23 | Cohort 2 n = 54 | p |
|---|---|---|---|---|
| AKIN Stage at Enrollment | | | | |
| AKIN I | 41 (53. %) | 14 (60.9%) | 27 (50%) | 1.00 |
| AKIN II | 36 (46.7%) | 9 (39.18%) | 27 (50%) | |
| Outcomes | | | | |
| Death | 16 (20.7%) | 8 (34.8%) | 8 (14.8%) | 0.07 |
| AKIN Stage III | 25 (32.4%) | 11 (47.8%) | 14 (25.9%) | 0.07 |
| RRT | 11 (14.2%) | 5 (21.7%) | 6 (11.1%) | 0.29 |
| Death/AKIN III | 32 (41.6%) | 13 (56.5%) | 19 (35.2%) | 0.13 |

All data presented as mean ± s.e. unless otherwise indicated. CKD = chronic kidney disease, CHF = congestive heart failure, DM = diabetes mellitus, NSAIDs = non-steroidal anti-inflammatory drugs, CV SOFA = cardiovascular sequential organ failure assessment, APACHE = acute physiology and chronic health evaluation, FeNa = fractional excretion of sodium, RRT = renal replacement therapy. RPP = renal perfusion pressure.
*FeNa not assessed on 29 patients since GW USS already ≥2 at the time of assessment Outcomes The primary outcome was the progression to AKIN stage III (need for RRT, increase in serum creatinine of 300% over baseline, urine output of 0.3 cc/kg/hour×24 hrs) within 14 days of FST. The secondary outcome was the composite of achieving stage AKIN III or death within 14 days of the FST.

Statistics

The distribution of demographic and clinical variables was assessed. Differences between proportions of patients with certain characteristics were assessed with chi-square, Fisher exact test, student t-test, and Mann-Whitney test as appropriate. The primary analysis was to assess the urine output response to the FST which was determined by assessing the area under the curve (AUC) receiver operating characteristics comparing the primary endpoint of progression to AKIN stage III and the secondary endpoint of death/AKIN III within 14 days of the FST.

Multivariable logistic regression was used to create three models. Model 1 is a clinical model using APACHE II score, baseline UFR, baseline eGFR, and AKIN stage II at study entry. Model 2 entered all univariate variables with a difference <0.10, as covariates. Model 3 is a multivariate backward elimination logistic regression. All means are reported+s.e. unless otherwise specified. Statistical analysis was performed using SPSS 18.0 (Chicago, Ill).

TABLE 2

Multivariable Logistic Regression for Progression to AKIN Stage III

| Variable | Odds Ratio | 95% CI | p value |
|---|---|---|---|
| APACHE II Score | 1.05 | 0.97-1.13 | 0.25 |
| Two Hour UO | 0.97 | 0.95-0.99 | 0.02 |
| Baseline eGFR | 0.99 | 0.97-1.01 | 0.45 |
| AKIN Stage II | 4.1 | 1.1-14.1 | 0.03 |

TABLE 3

Multivariable Logistic Regression for Progression to AKIN Stage III

| Variable | Odds Ratio | 95% CI | p value |
|---|---|---|---|
| Two Hour UO | 0.98 | 0.96-0.99 | 0.05 |
| GW USS Cast Score | 1.08 | 0.62-1.9 | 0.79 |

TABLE 3-continued

Multivariable Logistic Regression for Progression to AKIN Stage III

| Variable | Odds Ratio | 95% CI | p value |
|---|---|---|---|
| APACHE II Score | 1.1 | 0.96-1.1 | 0.42 |
| AKIN Stage II | 3.0 | 0.86-10.5 | 0.09 |
| Baseline UFR | 0.98 | 0.95-1.01 | 0.07 |

TABLE 4

Backward Elimination Logistic Regression to Predict Progression to AKIN III

| Variable | Odds Ratio | 95% CI | p value |
|---|---|---|---|
| Two Hour UO | 0.98 | 0.96-0.99 | 0.04 |
| AKIN Stage II | 4.7 | 1.7-12.8 | 0.003 |
| Baseline UFR | 0.98 | 0.97-1.01 | 0.08 |

Age, APACHE II score, CV SOFA score, baseline eGFR, post-cardiac surgery, sepsis, GW USS cast score, CHF, DM, HTN, AKIN stage II, Baseline UFR, and Two Hour UO placed into a backward elimination logistic regression.

Two hour UO is for each 10 cc of UO in increase. GW USS=George Washington Urinary Sediment Score, UFR=urine flow rate (ml/hr), CHF=history of congestive heart failure, DM=history of diabetes mellitus, and HTN=history of hypertension, Baseline eGFR=MDRD calculated eGFR.

Results

A total of 77 patients, 23 patients from Cohort 1 and 54 from Cohort 2, were assessed. The mean age was 65.3±1.6 years, 42.8% were male. Among the patients, 44 (57.1%) were African-American, 23 (29.9%) were Caucasian, and 10 (13%) were Hispanic (Table 1). Of the 77 patients, 25 (32.4%) met the primary outcome of AKIN Stage III and 16 (20.7%) died. Of the total cohort, 32 (41.6%) met the secondary composite endpoint of AKIN III or death within 14 days of the FST. Of the 25 patients who progressed to AKIN stage III, 11 (44.0%) received RRT.

In the overall cohort, 24 patients (31%) had chronic kidney disease (CKD). The number of patients with diabetes mellitus (DM), hypertension (HTN), and congestive heart failure (CHF) were 35(44%), 60 (78%), and 25 (33%), respectively. The proportion of patients with CKD, HTN, CHF, and DM was not statistically different between progressors and non-progressors (Table 1). There was no difference in the prevalence of sepsis or recent cardiac surgery in those who did and did not progress. Baseline serum albumin and serum lactate concentrations were not different between those who did and did not progress (data not shown). The mean cardiovascular SOFA score was 1.16 (0.3) and the mean APACHE II score was 17.8 (1.11); there was no difference between progressors or non-progressors.

The baseline urine flow rate (UFR) for the 6 hours before the FST was 74.2 (11.6) ml/hr. The baseline UFR was 95.7 (16.3) and 29.7 (4.2) in the non-progressor group and in the progressor group, respectively (p<0.01). Within the cohort of patients, 36 (46.8%) had AKIN stage II by either urine output (UO) or Scr criteria at time of enrollment. There were fewer patients with AKIN stage II amongst non-progressors 18 (34.6%) as compared to progressors 18 (72%) (p<0.003). In the overall cohort, the mean cast score was 2.3 (0.13). Non-progressors had a GW USS of 2.1 (0.16) compared to progressors who had a mean GW USS of 2.7 (0.23) (p=0.05). The ROC AUC for GW USS to predict AKIN III was 0.63 (0.07).

FST urine output (for each increase of 10 ml of UO) was predictive of non-progression to AKIN stage III when baseline patient imbalances were placed into a multivariate logistic analysis (OR-0.98, 0.96-0.99, p=0.05).

Furosemide Stress Test Characteristics

The FST was well tolerated with no episodes of hypotension or any other adverse event deemed attributable to the test. The maximum UFR was within the first two to three hours. For each hourly interval, progressors to AKIN stage III had a lower UFR response compared to non-progressors (p<0.001). There was no difference between the UFR of patients who were furosemide naïve and those who were not.

It was found that the sum of the first two hours of UO after the FST had the highest AUC to predict the primary outcome (0.87 in both the test and validation cohort). The two hour UO of 200 ml or less had the best sensitivity and specificity to predict the primary outcome.

TABLE 5

Furosemide Stress Test Effect on Urine Flow

| Time Period | Combined n = 77 | Furosemide Naive n = 29 | Non-naive N = 48 | p |
|---|---|---|---|---|
| Hour 1 (ml) | 251 (35.2) | 331 (68.5) | 258 (37.2) | 0.11 |
| Hour 2 (ml) | 296 (35.8) | 348 (66.6) | 264 (40.9) | 0.29 |
| Hour 3 (ml) | 246 (26.6) | 285 (52.1) | 223 (28.6) | 0.30 |
| Hour 4 (ml) | 207 (24.1) | 240 (48.6) | 188 (25.4) | 0.35 |
| Hour 5 (ml) | 175 (18.6) | 204 (35.9) | 157 (22.5) | 0.26 |
| Hour 6 (ml) | 155 (17.4) | 167 (33.6) | 147 (19.6) | 0.61 |

Urine volumes shown as mean (s.e.).

Discussion

In this pilot study using a test and validation cohort, it is demonstrated that the FST is feasible and well tolerated in critically ill patients with AKI. Furosemide administration can be associated with vasodilation and hypotension, but these complications were not observed in this study, perhaps because of careful measures taken to ensure that the patients were deemed clinically well-resuscitated and when appropriate, received isovolemic replacement of UO with isotonic fluids.

The performance of the FST to predict the primary outcome was robust and consistent in both the test and the validation cohort, with a range in ROC AUC of 0.82 to 0.87. The performance of the FST was comparable or exceeded the performance of several AKI biomarkers in predicting AKI progression. The first two hour interval had the best predictive capacity (0.87), and this interval corresponds with the maximum urinary flow rate in response to the FST. When specific UO cut-offs were assessed, it was determined that the two hour UO of 200 cc offered the best combination of sensitivity and specificity (87.1% and 84.1%, respectively).

Previous investigators have shown that in patients without AKI, the maximum diuretic effect of furosemide occurs within the first three hours. Similar kinetics were observed in this study. Patients that progressed to AKIN III compared to those that did not progress were similar in age, CV SOFA score, APACHE II score, baseline eGFR, and had a similar incidence of comorbidies. Nephrotoxic exposures and clinical phenotype was also similar between progressors and non-progressors. Not surprisingly, the progressor group tended to have more patients with AKIN stage II, a lower baseline UFR, and a higher mean cast score prior to FST. In multivariable analyses, UO response to FST was still statistically associated with progression to AKIN stage III, even when these variables were placed into the model.

In this study, we have used the FST as a functional test to predict progressive AKI. Urine biomarkers have been used previously to predict worsening AKI. The predictive value of the FST compares favorably with other recent biomarker studies. While the findings in this study show acceptable performance metrics for the FST, the use of the FST in patients who are not appropriately resuscitated can be potentially deleterious. We cannot overemphasize the point that patients need to be euvolemic before undertaking any type of furosemide challenge, and that volume replacement is mandatory in patients who are not obviously volume overloaded, as the mean UO in response to the challenge was over 1.3 liters in 6 hours. In addition, the FST should be conducted in an appropriate clinical setting where UO, heart rate, and blood pressure can be monitored frequently.

Example 2

Patients with acute decompensated (ADHF) heart failure typically have oliguria and reduced renal blood flow (RBF). As a consequence, these patients can have concomitant AKI. In order to determine the severity of tubular damage from AKI, the FST can be used (with biomarkers of course). Patients with severe ADHF who have diminished RBF will have a poor response to an FST (not much urine output). The FST can be used specifically to assess early in the course of ADHF to assess the degree of diuretic resistance to loop diuretic. Instead of stepping up the dose of diuretic, then realizing the patient us resistant, the FST enables the use of substantial amounts of loop diuretic, and if the urine output response is very brisk, intravenous fluid replacement can be done to prevent excessive volume depletion. As an example, if a patient has a response to 600 cc per hour of UO as a response to the dose of furosemide, 400 cc/hr of intravenous fluid can be returned per hour to allow a nice safe net negative of 200 cc/hour. This allows safe diuresis and the brisk response to furosemide diagnoses the patient as being diuretic responsive.

In addition, in these patients the measurement of furosemide in the urine can be very useful. Patients with decreased renal perfusion have 'pre-renal' physiology. In a pre-renal state (e.g. ADHF, volume depletion), patients have adequate RBF to provide energy for the renal tubule (hence the ability for the kidney to resorb sodium), but not enough RBF to maintain GRF. In this circumstance, the renal tubule should be able to transport furosemide into the tubule, but the response to the FST will still be poor to modest. This occurs because most of the tubular fluid is resorbed in the proximal tubule, which prevents the distal tubule from increasing urine flow. In this scenario, the FST would produce a modest increase in UO compared to baseline with a significant amount of furosemide excreted in the urine. If however, the proximal tubule is damage, the response to the FST will be poor to modest, with very little furosemide in the urine.

|  | Shock (Very Low RBF) | Pre-Renal | Acute Tubular Injury |
|---|---|---|---|
| Baseline UFR | Oligo-anuric | Oliguric | Normal to Oliguria |
| Post-FST UFR | Oliguric | Modest to Brisk | Oliguric to Moderate |
| Furosemide in Urine | None-Little | Significant portion of iv dose recovered in urine | Little/Some |

For AKI, the measurement of the diuretic in the urine can help identify where the injury in the tubule is located. See table above. The presence of furosemide in conjunction with the urine output response can help delineate if the renal proximal tubule is dysfunctional, or if the distal portions of the tubule can respond to furosemide.

In CKD, the degree of fibrosis in the interstitium is highly predictive of outcome. Thus, the response to FST in a patient with CKD correlates with the degree of fibrosis and tubular disease. When a substantial dose of furosemide is administered, all nephrons that can respond to furosemide should be exposed. Thus, a patient with healthy tubules has a brisk response to FST. Returning fluid to the patient during the FST is the only safe way to do this assessment. In addition, the measurement of furosemide in the urine can help determine how much of tubular dysfunction is in the proximal tubule. This CKD test can be done in conjunction with other diuretic and biomarkers.

|  | CKD (good prognosis) | CKD (proximal tubule intact) Intermediate Progosis | CKD (proximal tubule damaged) PoorProgosis |
|---|---|---|---|
| Baseline UFR | normal | normal | Normal to Oliguria |
| Post-FST UFR | Brisk | Moderate to Brisk | Moderate |
| Furosemide in Urine | Significant (>50% of IV dose recovered) | Moderate (<30-50% of IV dose recovered) | Little/Some (<30% of IV dose recovered) |

Example 3

References

Bellomo R, Kellum J A, Ronco C, (2012) Acute kidney injury. Lancet 380: 756-766
Coca S G, Singanamala S, Parikh C R, (2012) Chronic kidney disease after acute kidney injury: a systematic review and meta-analysis. Kidney Int 81: 442-448
Hsu R K, McCulloch C E, Dudley R A, Lo L J, Hsu C Y, (2013) Temporal changes in incidence of dialysis-requiring AKI. J Am Soc Nephrol 24: 37-42
Gibney N, Hoste E, Burdmann E A, Bunchman T, Kher V, Viswanathan R, Mehta R L, Ronco C, (2008) Timing of initiation and discontinuation of renal replacement therapy in AKI: unanswered key questions. Clin J Am Soc Nephrol 3: 876-880
Seabra V F, Balk E M, Liangos O, Sosa M A, Cendoroglo M, Jaber B L, (2008) Timing of renal replacement therapy initiation in acute renal failure: a meta-analysis. Am J Kidney Dis 52: 272-284
Koyner J L, Garg A X, Coca S G, Sint K, Thiessen-Philbrook H, Patel U D, Shlipak M G, Parikh C R, (2012) Biomarkers predict progression of acute kidney injury after cardiac surgery. J Am Soc Nephrol 23: 905-914
Chawla L S, Kellum J A, (2012) Acute kidney injury in 2011: Biomarkers are transforming our understanding of AKI. Nat Rev Nephrol 8: 68-70
Bonventre J V, (2007) Diagnosis of acute kidney injury: from classic parameters to new biomarkers. Contrib Nephrol 156: 213-219
Devarajan P, (2007) Emerging biomarkers of acute kidney injury. Contrib Nephrol 156: 203-212
Doi K, Noiri E, Sugaya T, (2010) Urinary L-type fatty acid-binding protein as a new renal biomarker in critical care. Curr Opin Crit Care 16: 545-549
Hasannejad H, Takeda M, Taki K, Shin H J, Babu E, Jutabha P, Khamdang S, Aleboyeh M, Onozato M L, Tojo A, Enomoto A, Anzai N, Narikawa S, Huang X L, Niwa T, Endou H, (2004) Interactions of human organic anion transporters with diuretics. J Pharmacol Exp Ther 308: 1021-1029
Bowman R H, (1975) Renal secretion of [35-S]furosemide and depression by albumin binding. Am J Physiol 229: 93-98
Burg M, Stoner L, Cardinal J, Green N, (1973) Furosemide effect on isolated perfused tubules. Am J Physiol 225: 119-124
Dirks J H, Seely J F, (1970) Effect of saline infusions and furosemide on the dog distal nephron. Am J Physiol 219: 114-121
Brater D C, Anderson S A, Strowig S, (1979) Azosemide, a "loop" diuretic, and furosemide. Clin Pharmacol Ther 25: 435-439
Mehta R L, Kellum J A, Shah S V, Molitoris B A, Ronco C, Warnock D G, Levin A, (2007) Acute Kidney Injury Network: report of an initiative to improve outcomes in acute kidney injury. Crit Care 11: R31
Alge J L, Karakala N, Neely B A, Janech M G, Tumlin J A, Chawla L S, Shaw A D, Arthur J M, (2013) Urinary Angiotensinogen and Risk of Severe AKI. Clin J Am Soc Nephrol 8: 184-193
Chawla L S, Dommu A, Berger A, Shih S, Patel S S, (2008) Urinary sediment cast scoring index for acute kidney injury: a pilot study. Nephron Clin Pract 110: c145-150
Loon N R, Wilcox C S, Unwin R J, (1989) Mechanism of impaired natriuretic response to furosemide during prolonged therapy. Kidney Int 36: 682-689
Arendshorst W J, Finn W F, Gottschalk C W, (1975) Pathogenesis of acute renal failure following temporary renal ischemia in the rat. Circ Res 37: 558-568
Bird J E, Milhoan K, Wilson C B, Young S G, Mundy C A, Parthasarathy S, Blantz R C, (1988) Ischemic acute renal failure and antioxidant therapy in the rat. The relation between glomerular and tubular dysfunction. J Clin Invest 81: 1630-1638
Chennavasin P, Seiwell R, Brater D C, Liang W M, (1979) Pharmacodynamic analysis of the furosemide-probenecid interaction in man. Kidney Int 16: 187-195

Baek S M, Brown R S, Shoemaker W C, (1973) Early prediction of acute renal failure and recovery. I. Sequential measurements of free water clearance. Ann Surg 177: 253-258

Hall I E, Coca S G, Perazella M A, Eko U U, Luciano R L, Peter P R, Han W K, Parikh C R, (2011) Risk of poor outcomes with novel and traditional biomarkers at clinical AKI diagnosis. Clin J Am Soc Nephrol 6: 2740-2749

Koyner J L, Vaidya V S, Bennett M R, Ma Q, Worcester E, Akhter S A, Raman J, Jeevanandam V, O'Connor M F, Devarajan P, Bonventre J V, Murray P T, (2010) Urinary biomarkers in the clinical prognosis and early detection of acute kidney injury. Clin J Am Soc Nephrol 5: 2154-2165

Heyman S N, Rosen S, Epstein F H, Spokes K, Brezis M L, (1994) Loop diuretics reduce hypoxic damage to proximal tubules of the isolated perfused rat kidney. Kidney Int 45: 981-985

Mehta R L, Pascual M T, Soroko S, Chertow G M, (2002) Diuretics, mortality, and nonrecovery of renal function in acute renal failure. Jama 288: 2547-2553

Ho K M, Power B M, (2010) Benefits and risks of furosemide in acute kidney injury. Anaesthesia 65: 283-293

Bagshaw S M, Gibney R T, McAlister F A, Bellomo R, (2010) The SPARK Study: a phase II randomized blinded controlled trial of the effect of furosemide in critically ill patients with early acute kidney injury. Trials 11: 50

Goldstein S L, Chawla L S, (2010) Renal angina. Clin J Am Soc Nephrol 5: 943-949

Bagshaw S M, Bennett M, Devarajan P, Bellomo R, (2012) Urine biochemistry in septic and non-septic acute kidney injury: a prospective observational study. J Crit Care Levey A S, Bosch J P, Lewis J B, Greene T, Rogers N, Roth D, (1999) A more accurate method to estimate glomerular filtration rate from serum creatinine: a new prediction equation. Modification of Diet in Renal Disease Study Group. Ann Intern Med 130: 461-470

Vincent J L, Moreno R, Takala J, Willatts S, De Mendonca A, Bruining H, Reinhart C K, Suter P M, Thijs L G, (1996) The SOFA (Sepsis-related Organ Failure Assessment) score to describe organ dysfunction/failure. On behalf of the Working Group on Sepsis-Related Problems of the European Society of Intensive Care Medicine. Intensive Care Med 22: 707-710

Knaus W A, Draper E A, Wagner D P, Zimmerman J E, (1985) APACHE II: a severity of disease classification system. Crit Care Med 13: 818-829

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for predicting progression to AKI stage III in patients with AKI stage I or II, wherein AKI stage is defined by the AKIN criteria, comprising:
   (a) selecting a critically ill patient diagnosed with AKI stage I or II, wherein the subject is euvolemic;
   (b) obtaining a urine sample from the subject for measuring a biomarker in the urine and measuring urine output,
   wherein the biomarker comprises one or more of Metalloproteinase inhibitor 2, Thrombospondin-1, Antileukoproteinase, Insulin-like growth factor-binding protein 7, Metalloproteinase inhibitor 4, Metalloproteinase inhibitor 1, Hyaluronic acid, Transmembrane glycoprotein NMB, Follistatin, Hepatocyte growth factor, Tumor necrosis factor receptor superfamily member 6, Growth-regulated alpha protein, C-C motif chemokine 24, Metalloproteinase inhibitor 3, C-X-C motif chemokine 6, Tumor necrosis factor receptor superfamily member 11B, Cystatin-C, Beta-2-microglobulin, Serum albumin, Clusterin, Interleukin-8, Neutrophil gelatinase-associated lipocalin, Interleukin-2 receptor alpha chain, Hepatitis A virus cellular receptor 1, Chitinase-3-like protein 1, or Serum creatinine, and wherein the result of the biomarker assay indicates that the subject has stage I or stage II acute kidney injury progression;
   (c) performing a diuretic stress test comprising:
      1. determining the baseline urine output for the subject,
      2. administering a diuretic intravenously to the subject in an amount effective to cause diuresis; and
      3. determining the diuretic-induced urine output for the first 2 hours after administering the diuretic intravenously;
   (d) identifying the subject at risk for progressing to AKI stage III in 14 days and in need of treatment, when the diuretic-induced urinary output is 200 mL or less for the first two hours after administering of the diuretic;
   (e) administering treatment to the identified patient of (d) wherein the treatment comprises one or more of initiating renal replacement therapy, withdrawing delivery of compounds that are known to be damaging to the kidney, and modifying diuretic administration, wherein the diuretic is a loop diuretic selected from the group consisting of furosemide, bumetanide, ethacrynic acid, torsemide, mannitol, torsemidehydrochlorothiazide, bendroflumethiazide, hydroflumethiazide, chlorothiazide, polythiazide, trichlormethiazide, cyclopenthiazide, methyclothiazide, cyclothiazide, and mebutizide, and wherein the biomarker comprises one or more of Metalloproteinase inhibitor 2, Thrombospondin-1, Antileukoproteinase, Insulin-like growth factor-binding protein 7, Metalloproteinase inhibitor 4, Metalloproteinase inhibitor 1, Hyaluronic acid, Transmembrane glycoprotein NMB, Follistatin, Hepatocyte growth factor, Tumor necrosis factor receptor superfamily member 6, Growth-regulated alpha protein, C-C motif chemokine 24, Metalloproteinase inhibitor 3, C-X-C motif chemokine 6, Tumor necrosis factor receptor superfamily member 11B, Cystatin-C, Beta-2-microglobulin, Serum albumin, Clusterin, Interleukin-8, Neutrophil gelatinase-associated lipocalin, Interleukin-2 receptor alpha chain, Hepatitis A virus cellular receptor 1, Chitinase-3-like protein 1, and Serum creatinine.

2. The method of claim 1, wherein the biomarker comprises Metalloproteinase inhibitor 2 and Insulin-like growth factor-binding protein 7.

3. The method of claim 1, wherein prior to step c, the method further comprises measuring the biomarker to obtain an assay result and correlating the result to diagnosis of AKI stage I or II based on a diagnostic threshold to aid diagnosis.

4. The method of claim 3, wherein the biomarker comprises Metalloproteinase inhibitor 2 and Insulin-like growth factor-binding protein 7.

5. The method of claim 1, wherein the diuretic is furosemide.

6. The method of claim 1, wherein the treatment comprises initiating renal replacement therapy.

\* \* \* \* \*